United States Patent [19]

Garabedian et al.

[11] Patent Number: 4,632,772

[45] Date of Patent: Dec. 30, 1986

[54] MILD ANTIMICROBIAL DETERGENT COMPOSITION

[75] Inventors: Michael E. Garabedian, Arlington; Jerry L. Tims, Euless, both of Tex.

[73] Assignee: Dexide, Inc., Fort Worth, Tex.

[21] Appl. No.: 350,591

[22] Filed: Feb. 22, 1982

[51] Int. Cl.[4] .......................... C11D 3/44; C11D 3/48
[52] U.S. Cl. .................................... 252/106; 252/548; 252/558
[58] Field of Search ............... 252/106, 554, 548, 107, 252/DIG. 5, 558; 424/347, 358

[56] References Cited

U.S. PATENT DOCUMENTS

| | | | |
|---|---|---|---|
| Re. 28,778 | 4/1976 | Winicov et al. | 252/106 |
| 2,303,932 | 12/1942 | Guild | 252/142 X |
| 3,063,895 | 11/1962 | Pearson et al. | 424/37 |
| 3,326,808 | 6/1967 | Noseworthy | 252/106 |
| 3,355,387 | 11/1967 | Hinkel | 252/106 |
| 3,574,821 | 4/1971 | Pfirrman et al. | 514/635 |
| 3,597,360 | 8/1971 | Collins et al. | 252/106 |
| 3,629,454 | 12/1971 | Barr et al. | 252/106 X |
| 3,649,543 | 3/1972 | Cahn et al. | 252/526 |
| 3,813,350 | 5/1974 | Kelly et al. | 252/547 |
| 3,824,190 | 7/1974 | Winicov et al. | 252/106 |
| 3,875,071 | 4/1975 | Grand | 252/106 |
| 3,944,663 | 3/1976 | Weiss et al. | 424/78 |
| 3,950,532 | 4/1976 | Bouillon et al. | 424/275 |
| 4,010,252 | 3/1977 | Hewitt | 424/47 |
| 4,122,085 | 10/1978 | Douglass | 252/106 X |
| 4,142,985 | 3/1979 | Louderback et al. | 252/106 |
| 4,242,365 | 12/1980 | Hasegawa et al. | 426/438 |

FOREIGN PATENT DOCUMENTS

| | | |
|---|---|---|
| 743984 | 1/1956 | United Kingdom . |
| 1052704 | 12/1966 | United Kingdom . |

OTHER PUBLICATIONS

*Chemical Week*, Apr. 16, 1951, pp. 72, 74.
Cosmetics Science and Technology (1957), pp. 403, 406 and 408.

*Primary Examiner*—Prince E. Willis
*Attorney, Agent, or Firm*—Richards, Harris, Medlock & Andrews

[57] ABSTRACT

An antimicrobial composition which exhibits excellent mildness characteristics comprising from about 11-17% of an ionic detergent, from about 1.1 to about 7% foaming agents, from about 2.2 to 14% of a moisturizer/emollient agent, from about 0.1 to about 0.7% of a thickener, from about 1.5 to about 3.75% of an active antimicrobial agent, sufficient acid if necessary to adjust the pH in the range of 4.5 to 6.5, and adding water to 100%.

2 Claims, No Drawings

MILD ANTIMICROBIAL DETERGENT COMPOSITION

TECHNICAL FIELD

This invention relates to antimicrobial detergent compositions and more particularly to a mild antimicrobial detergent composition suitable for use as a surgical scrub which exhibits unexpected mildness to the human skin.

BACKGROUND ART

The present invention relates to a mild antimicrobial detergent composition which is particularly suited for use as a surgical scrub. To be suitable for use as a surgical scrub, a composition must be antiseptic as well as mild.

Effective antiseptic or disinfectant compositions can be formed by combining a detergent with an antimicrobial agent. Thus, antiseptic cleaning compounds can be formulated rather easily; however, many such compositions are not suitable for use in contact with human skin. Where the composition is intended for use as a surgical scrub mildness is an important consideration. Mildness as used herein indicates the composition does not cause excessive irritation of the skin, such as erythema, from the contact of the composition with the skin.

In a majority of cases, skin irritations can be attributed to contact of the skin with a detergent. It is believed that skin irritation results partly due to a nature of the detergent itself and, in part, due to the action of the detergent in weakening the resistance of the skin. The degree of irritation may vary significantly with the detergent, the individual user, the length of contact and the conditions of contact. In many cases the degree of irritation is also affected by other chemicals which are combined with a detergent.

While the cause of skin irritation is not clearly understood, it is believed that detergents have a denaturing effect on the keratin layer of the skin. Thus, chemicals which normally do not irritate the skin when combined with a detergent can penetrate the skin and cause irritation. Furthermore, some chemicals when combined with a detergent may be more readily absorbed by the skin. The absorption of the other chemicals is generally undesirable, especially those which are harmful or toxic to the body.

Numerous attempts have been made to develop additives or formulations which reduce or eliminate skin irritation. Thus far there has been limited success in providing a mild surgical scrub composition. Surgical scrub procedures and surgical techniques are highly conducive to the development of erythema and other irritations. All personnel involved in surgical procedures employ the surgical scrub in preparation for surgery. Frequently, the same individual will scrub three to five times on a single day. A typical surgical scrub involves placing an antimicrobial cleansing solution on the hand. Commonly a brush or sponge is used and the arms from the elbows to the fingertips are scrubbed thoroughly for as long as ten minutes. Thus, the epidermal layers of the skin are subjected to significant rubbing and aggravation. After the arms and hands have been scrubbed they are rinsed, dryed and placed into rubber gloves. The rinse is often not complete and residual detergent and/or antimicrobial compounds are left on the skin. Many times, the hands remain gloved for as long as six hours. During this time the hand perspires and the pores can open and enlarge, thereby allowing residual detergent and/or antimicrobial compounds to penetrate the skin. This in turn can create topical skin irritations. The likelihood of irritation or erythema increases with the frequency one performs the surgical scrub procedure. Thus, it is important that surgical scrub compositions be very mild.

In addition, the surgical scrub can be even more hazardous where the antimicrobial agent is toxic to humans. For example, hexachlorophene (HCP) is a known antimicrobial agent and is utilized in commercial antibacterial skin cleansers. These HCP containing cleansers have been utilized in surgical scrub procedures. Evidence has come to light which demonstrates that HCP when used in topical products can be absorbed by the body in dangerously high levels. Hexachlorophene has been associated with brain stem damage, as well as central nervous system damage. The Food and Drug Administration and the medical community have discouraged the use of HCP because of its toxicity.

The two prevalent surgical scrubs contain either iodophor or hexachlorophene. To discontinue the use of hexachlorophene would cause a gap in products available as a surgical scrub, because a substantial portion of the population, perhaps up to 20%, is allergic to surgical scrubs containing iodine in the form of iodophor.

Thus, a need has arisen for a surgical scrub composition which is very mild and which preferably contains an antimicrobial agent which is nontoxic or exhibits low toxicity to humans, and to which few individuals are allergic.

DISCLOSURE OF THE INVENTION

The present invention relates to a surgical scrub composition containing antimicrobial agents which is very mild. More specifically, the antimicrobial composition of the subject invention comprises from about 11 to about 17% of a surfactant, from about 1.1 to 7% of a foam builder, from about 2.2 to 14% of a moisturizer/emollient, from about 1.5 to about 3.75% of active antimicrobial agent, from about 0.12 to about 0.7% of a thickener, a small amount of acid to adjust the pH to the range of 4.5 to about 6.5, and the balance water.

A preferred antimicrobial composition comprises from 12 to about 17% alkyl aryl ethoxylated sulfonate, from about 1.5 to about 4% lauric diethanol amide, from about 0.3 to about 2% myristic diethanol amide, from about 4 to about 9% petrolatum, from about 0.1 to about 0.4 ethylene glycol monostearate, from about 0.5 to about 1.2% lanolin alcohol, from about 2 to about 3.25% parachloro metaxylenol (hereinafter "PCMX"), sufficient acid to adjust the pH in the range of 4.5 to 6.5, and the remainder being water.

DETAILED DESCRIPTION

The surgical scrub compositions of the present invention exhibit unexpected mildness. This unexpected mildness is not anticipated from results of animal tests. It is a practice in the industry to first test antibacterial compositions on animals to test for skin irritation. Two such tests are set forth in the Code of Federal Regulations, Title 16, Sections 1500.41 and 1500.42. A method of testing primary irritant substances is set forth in 16 C.F.R. §1500.41. A test for eye irritants is provided in 16 C.F.R. §1500.42.

The test described for primary irritant in 16 C.F.R. §1500.41 calls for a patch-test technique on abraded and intact skin of a rabbit, clipped free of hair. A minimum of six subjects are used. The substance to be tested is introduced under a surgical gauze which is secured by adhesive tape. The entire trunk of the animal is then wrapped with an impervious material, such as rubberized cloth, for 24 hours. The rubberized cloth serves to maintain the patch in place and retards the evaporation of volatile substances. After 24 hours of exposure, the patches are removed and the results are evaluated on the basis of the designated values in the following table:

| Skin Reaction | Value[1] |
|---|---|
| Erythema and eschar formation: | |
| No erythema | 0 |
| Very slight erythema (barely perceptible) | 1 |
| Well-defined erythema | 2 |
| Moderate to severe erythema | 3 |
| Severe erythema (beet redness) to slight eschar formations (injuries in depth) | 4 |
| Edema formation: | |
| No edema | 0 |
| Very slight edema (barely perceptible) | 1 |
| Slight edema (edges of area well defined by definite raising) | 2 |
| Moderate edema (raised approximately 1 millimeter) | 3 |
| Severe edema (raised more than 1 millimeter and extending beyond the area of exposure) | 4 |

[1]The "value" recorded for each reading is the average value of the six or more animals subject to the test.

Readings are again made at the end of 72 hours (48 hours after the first reading).

An equal number of exposures are made on areas of the skin that have previously been abraded. The abrasions are minor incisions through the stratum corneum, but not sufficiently deep to disturb the derma or to produce bleeding. The reactions on the abraded skin are reported at 24 hours and 72 hours as described before. The values for erythema and eschar formation at 24 hours and 72 hours for intact skin and the values on abraded skin at 24 hours and 72 hours are added. Similarly, the values for edema formation at 24 hours and 72 hours for intact and abraded skin are added. The total of the eight values is divided by four to give the primary irritation score, for example:

| Skin reaction | Exposure time (hours) | Evaluation value |
|---|---|---|
| Erythema and eschar formation: | | |
| Intact skin | 24 | 2 |
| " | 72 | 1 |
| Abraded skin | 24 | 3 |
| " | 72 | 2 |
| Subtotal | | 8 |
| Edema formation: | | |
| Intact skin | 24 | 0 |
| " | 72 | 1 |
| Abraded skin | 24 | 1 |
| " | 72 | 2 |
| Subtotal | | 4 |
| Total | | 12 |

Thus, the primary irritation score for the example is 3, i.e. 12 divided by 4 which equals 3.

The test for eye irritants is in general as follows. Six albino rabbits are used for each substance. Extraneous material such as saw dust, wood chips, or other materials which may produce eye irritation are excluded. Both eyes of each animal in the test group are examined before testing to assure the eyes are without defect or irritation. Test material is placed in one eye of each animal by pulling the lower lid away from the eyeball to form a cup into which about 0.1 milliliters of test substance is dropped. The untreated eye serves as a control. The eyes are examined and the grade of ocular reaction is recorded at 24, 48 and 72 hours. Reading of reactions is facilitated by the use of a binocular loupe, hand slit lamp, or other means. The animal shall be considered as exhibiting a positive reaction if the test substance produces at any of the readings ulceration of cornea (other than fine stippling), or opacity of the cornea (other than a slight dulling of the normal luster), or inflammation of the iris (other than a slight deepening of the folds (or orugae) or a slight circumcorneal injection of the blood vessels), or if such substance produced in the conjunctivae (excluding the cornea and the iris) an obvious swelling with partial eversion of the lids for a diffuse crimson-red with individual vessels not easily discernable. The test is considered positive if four or more of the animals exhibit a positive reaction. If only one animal exhibits a positive reaction the test is regarded as negative. If two or three animals give a positive reaction the test is repeated using a different group of animals. The second test is considered positive if three or more of the animals exhibit a positive reaction. If only one or two of the animals in the second test exhibit positive reaction, the test shall be repeated with a different group of six animals. Should a third test be needed, the substance will be regarded as an irritant if any animal exhibits a positive reaction.

The primary irritant test described above closely approximates the conditions present in surgical scrub procedures. In surgical scrubs the residual detergent and/or antimicrobial agent is maintained in contact with the skin by the rubber surgical glove. Of course, one would expect a composition with a primary irritant score of from 0 to 1 would be most suitable for use as a surgical scrub. However, the composition of the present invention exhibited a primary irritant score greater than 3.0 in the rabbit test but nevertheless did not irritate human users. Whereas, compositions with primary irritant scores of from 0 to 1 in the rabbit test were irritating to human users.

The antimicrobial composition of the present invention has the following general formula:

| INGREDIENT | WEIGHT PERCENT |
|---|---|
| Anionic surfactant | 11-17 |
| Foam builder | 1.1-7 |
| Moisturizer/emollient | 2.2-14 |
| Thickener | 0.1-0.7 |
| Active antimicrobial agent | 1.5-3.75 |
| Acid | sufficient to adjust pH in the range of 4.5-6.5 |
| Water | sufficient amount to total 100% |

The surfactant may be any mild anionic surfactant. Suitable surfactants include octyl phenoxy ethyleneoxy sulfonate, nonyl phenoxy ethyleneoxy sulfonate. The ethyleneoxy content should be in the range of 2-14 molecules. The cation portion can be ammonium, sodium or potassium. The preferred surfactant is octyl phenoxy ethyleneoxy sulfonate (sodium salt). Preferably the surfactant is present in the range of from about 12 to 17%. The surfactant should be preferably used in an amount sufficient to maintain a stable emulsion.

The foam builder is a fatty acid alkanol amide. The fatty acid portion can be lauric, coco, myristic or stearic. Lauric ethanol amide is preferred. Most preferably the foam builder is a combination of lauric diethanol amide and myristic diethanol amide.

To prevent chapping of the skin a moisturizer/emollient is utilized. The moisturizer/emollient may be a vegetable, animal or mineral oil or a synthetic oil. Petrolatum is suitable. The function of the emollient/moisturizer is to replace the natural skin oils which are lost or, at least, partially removed by the cleansing action of the detergent. In addition, it also serves to dissolve and maintain the oil-soluble antiseptics in the emulsion. Suitable emollients include lanolin and derivatives of lanolin such as ethoxylated, acylated alcohol and surface active alcohol derivatives of lanolin. Lanolin cholesterol is suitable also. Preferably the moisturizer/emollient is a mixture of petrolatum and lanolin alcohol.

The active antimicrobial agent may be hexachorophene, para chloro meta xylenol, 4 hexylresorcinol, o-phenyl phenol, o-benzyl p-chorophenol. The preferred antimicrobial agent is para chloro meta xylenol.

To add stability to the emulsion a thickener is added. The thickener is a polyethylene glycol fatty acid ester of the general formula:

$$R_1OCH_2CH_2(OCH_2CH_2)_n-OR_2$$

where n equals 0 to 30; $R_1$ is lauric, myristic, palmitic, stearic or hydrogen; and $R_2$ is lauric, myristic, palmactic, stearic or hydrogen. $R_1$ and $R_2$ can be the same or a different radical. The preferred thickener is ethylene glycol monostearate.

The resulting final composition is then adjusted to a pH within the aforestated range from about 4.5 to about 6.5. Most preferably the pH is adjusted in the range of 5.0 to 6.0. Adjustment of the pH is desirable to avoid unnecessary irritation of the skin. To insure the pH is maintained within this range, small amounts (normally less than about 1.0%) of a nontoxic acidic substance may be added. Suitable acids include hydrochloric acid, sulfuric acid, phosphoric acid, citric acid, lactic acid, and gluconic acid, for example. Citric acid is preferred.

The water should be free of impurities. The water utilized is preferably processed such that it meets the bacteriological purity standards of the U.S. Pharmacopeia for purified water.

The preferred embodiments of the present invention have the following formula:

| COMPONENT | WEIGHT PERCENT | | |
|---|---|---|---|
| | SUITABLE | PREFERRED | MOST PREFERRED |
| alkyl aryl ethoxylated sulfonate | 11-17 | 12-17 | 14 |
| lauric diethanol amide | 1-4 | 1.5-4 | 2.5 |
| myristic diethanol amide | 0.1-3 | 0.3-2 | 0.5 |
| petrolatum | 2-12 | 4-9 | 7 |
| ethylene glycol monostearate | 0.1-0.7 | 0.1-0.4 | 0.3 |
| lanolin alcohol | 0.2-2 | 0.5-1.2 | 0.7 |
| parachloro metaxylenol | 1.5-3.75 | 2.0-3.25 | 3.25 |
| acid | sufficient to adjust pH in the of 5.0 to 6.0 | | |
| purified water | sufficient amount to yield a total of 100% | | |

The composition of the present invention may be made by a suitable emulsion process. The following batch process is suitable. The ingredients are placed in a suitable vessel such as a stainless steel tank equipped with a heating means, such as a heating jacket. The detergent is placed in the tank together with the liquid emollient/moisturizer ingredients, for example, lanolin alcohol as in the preferred embodiment. The mixture is agitated by a suitable means such as a stirrer. The mixture is heated in the range of from about 110° F. to about 170° F. Next the foam builders are added which in the preferred composition are lauric diethanol amide and myristic diethanol amide. Mixing and heating are continued. At this point the thickener is added which in the preferred composition is ethylene glycol stearate. Heating and stirring are continued. The remaining solid or semisolid moisturizer/emollient component is added. For example in the preferred embodiment petrolatum is melted, if required, and added to the heated and stirred system. With heating and stirring continuing water is added to make up about 90% of the final volume.

After water has been added to obtain about 90% of the final volume level, the active antimicrobial agent is added carefully so as to assure uniform dispersion throughout the system and to prevent caking and lumping while heating and stirring continue. In the preferred composition this ingredient is parachloro metaxylenol. While heat is maintained and stirring continues, the pH of the emulsion is adjusted, if necessary, to the ranges set forth above. Water is then added to adjust the final volume. During the above steps the temperature is maintained in the range of from about 105° F. to about 170° F.

The composition is mixed while heat is maintained until a smooth, homogeneous emulsion is obtained. Thereafter the antimicrobial composition may be packaged in suitable containers and allowed to cool to ambient temperature.

The invention is illustrated by the following examples, which are not to be construed in any way or manner as imposing limitations upon the scope thereof. It is understood that various other embodiments, modifications and equivalents will readily suggest themselves to those skilled in the art without departing from the spirit of the present invention and/or the scope of the appended claims. The following examples illustrate the unexpected mildness of the present composition.

Example 1 was formulated in such a manner as to provide for a very mild or nonirrritant antimicrobial composition. This formulation employed alpha-olefin sulfonate, a detergent which has found wide acceptance in shampoo products. When tested in accordance with the procedure of 16 C.F.R. §1500.41 on New Zealand white rabbits the test results were a primary irritation score of 0.8. Thus, the composition of Example 1 was judged to be a nonirritant by the test. The eye irritation test has conducted by the procedure of 16 C.F.R. §1500.42 also showed that it was nonirritant. From these findings it was believed that the composition of Example 1 would be extremely suitable as a surgical scrub. However, actual users reported that the composition was irritating and caused reactions such as erythemia.

Example 2 was formulated in accordance with the present invention according to the batch process described above. When this composition was tested by the primary skin irritation test with New Zealand white rabbits the results were the primary irritation score of 3.75 which indicated that it was a moderate to severe irritant. The eye irritation test showed that it was nonirritant. An oral toxicity test showed no observed toxicity at 2 ml/100 gm in mice administered by stomach tube.

to be a milder foam builder than sodium lauryl sulfonate. However, when the compositions of Examples 3 and 4 were tested in normal scrubbing procedures, both were judged as too irritating for use as a surgical scrub.

The composition of Example 1 was prepared by the emulsion method similar to that described herein. Examples 3 and 4 were prepared by dissolving the PCMX in the isopropyl alcohol followed by the addition of the surfactant, foaming agent and moisturizer/emollients. Water was added last.

Table I sets forth an example of the present invention in comparison to other formulations that were believed from test results to be suitable for use as surgical scrubs, but which did not meet with user acceptance.

TABLE I

| Ingredient | Example #1 | Example #2 | Example #3 | Example #4 |
|---|---|---|---|---|
| ANIONIC SURFACTANT | | | | |
| Sodium Alpha Olefin Sulfonate[1] | 10.0 | | | |
| Tall Oil Fatty Acid (Natural Soap)[2] | | | 10.0 | 10.0 |
| Alkyl Aryl Ethoxylated Sulfonate[3] | | 14.0 | | |
| FOAM BUILDER | | | | |
| Coco Diethanol Amide[4] | 1.0 | | | |
| Sodium Lauryl Sulfonate[5] | | | 2.4 | |
| Lauric Diethanol Amide[6] | | 2.5 | | 2.4 |
| Myristic Diethanol Amide[7] | | 0.5 | | |
| Lauryl Dimethyl Amine Oxide[8] | | | 0.6 | 0.6 |
| MOISTURIZER/EMOLLIENT | | | | |
| Glycerine[9] | 2.7 | | 2.0 | 2.0 |
| Petrolatum[10] | | 7.0 | | |
| Lanolin Alcohol[11] | | 0.7 | | |
| THICKENER | | | | |
| Ethylene Glycol Monostearate[12] | 0.6 | 0.3 | | |
| ACTIVE ANTIMICROBIAL AGENT PCMX[13] | 3.0 | 3.25 | 3.75 | 3.75 |
| ISOPROPYL ALCOHOL | | | 5.0 | 5.0 |
| ACID | | | | |
| Citric Acid | sufficient to pH 5.5 | sufficient to pH 5.5 | | |
| BASE | | | | |
| Potassium Hydroxide (45% solution) | | | 5.4 | 5.4 |
| WATER | remainder | remainder | remainder | remainder |

TABLE I FOOTNOTES
[1]Supplied by utilizing sufficient Bioterge AS-40 which is a 40% solution of sodium alpha olefin sulfonate sold by Stepan Chemical Co.
[2]Supplied in the form of Westvaco Diacid 1530 sold by Westvaco-Oleochemical Division.
[3]Supplied by utilizing sufficient TRITON X-200. TRITON X-200, sold by Rohm Hass Company, is a 28% aqueous solution of alkyl aryl ethoxylated sulfonate.
[4]Supplied in the form of Ninol 2012 Extra sold by Stepan Chemical Co.
[5]Supplied by utilizing sufficient Stepanol-Wac a 30% solution of sodium laryl sulfonate sold by Stepan Chemical Co.
[6]Supplied in the form of Monamid 716 sold by Mona Ind.
[7]Supplied in the form of Monamid 150 sold by Mona Ind.
[8]Supplied in the form of Ammonyx-LO, a 30% solution of lauryl diamethyl amine oxide, sold by Onyx Chemical.
[9]Supplied in the form of liquid glycerine sold by Dow Chemical Co.
[10]Supplied in the form of PENRECO SNOW sold by Penreco Inc.
[11]Supplied in the form of AMERCHOL L101 sold by Amerchol, Inc.
[12]Supplied in the form of PEGOSPERSE-50MS sold by Glyco Chemicals, in the composition of Example 2 and in Example 1 by using CPH-37-NA, sold by C. P. Hall Company.
[13]Supplied in the form of a fine powder sold under the trademark OTTOASEPT Xtra by Ottawa Chemical.

Thus, the animal tests of the composition of the present invention indicated that it would not be any mild antimicrobial composition suitable for surgical scrubs. However, actual user response to this formulation has been contrary to the projected results from the animal tests. Users have found the composition to be extremely mild and an excellent surgical scrub.

Examples 3 and 4 of Table I were in a manner designed to produce a mild surgical scrub. When the composition of Examples 3 and 4 were tested on humans employing a repeated insult patch test technique, less than 2% of the test subjects showed any sign of irritation. Thus, it was judged suitable for use as a surgical scrub. Example 4 differs from Example 3 in that Example 4 contains lauric diethanol amide in place of sodium lauryl sulfonate. Lauric diethanol amide is considered The composition of the present invention has been found effective as an antimicrobial agent. The composition of present invention is effective against *Escherichia colia, Pseudomonas aeruginosa, Steptococcus faecalis, Proteus vulgaris, Candida albicans,* and *Staphylococcus aureus.*

We claim:
1. An antimicrobial detergent composition comprising:
   (a) an alkylaryl ethoxylated sulfonate surfactant in an amount from 12 to 17 weight percent of total composition;
   (b) a foam builder in an amount from 1.8 to 6 weight percent of total composition, said foam builder comprising from about 1.5 to about 4.0 weight percent lauric diethanolamide, and from 0.3 to about 2.0 weight percent myristic diethanolamide, said percents based on weight of total composition;
(c) a moisturizer/emollient in an amount from 4.5 to 10.2 weight percent, said moisturizer/emollient comprising from about 4 to about 9.0 weight percent petrolatum, and from 0.2 to about 2.0 weight percent lanolin alcohol, said percents based on weight of total composition;

(d) an ethylene glycol monostearate thickener in an amount from 0.1 to 0.4 weight percent based on weight of total composition;
(e) parachloro metaxylenol from 2.0 to 3.25 weight percent based on total composition;
(f) plus sufficient acid to adjust the pH in the range of from about 4.5 to about 6.5; and
(g) the balance being water.

2. The composition of claim 1 wherein the pH is adjusted in the range of from 5.3 to 5.7.

* * * * *